Figure 1:
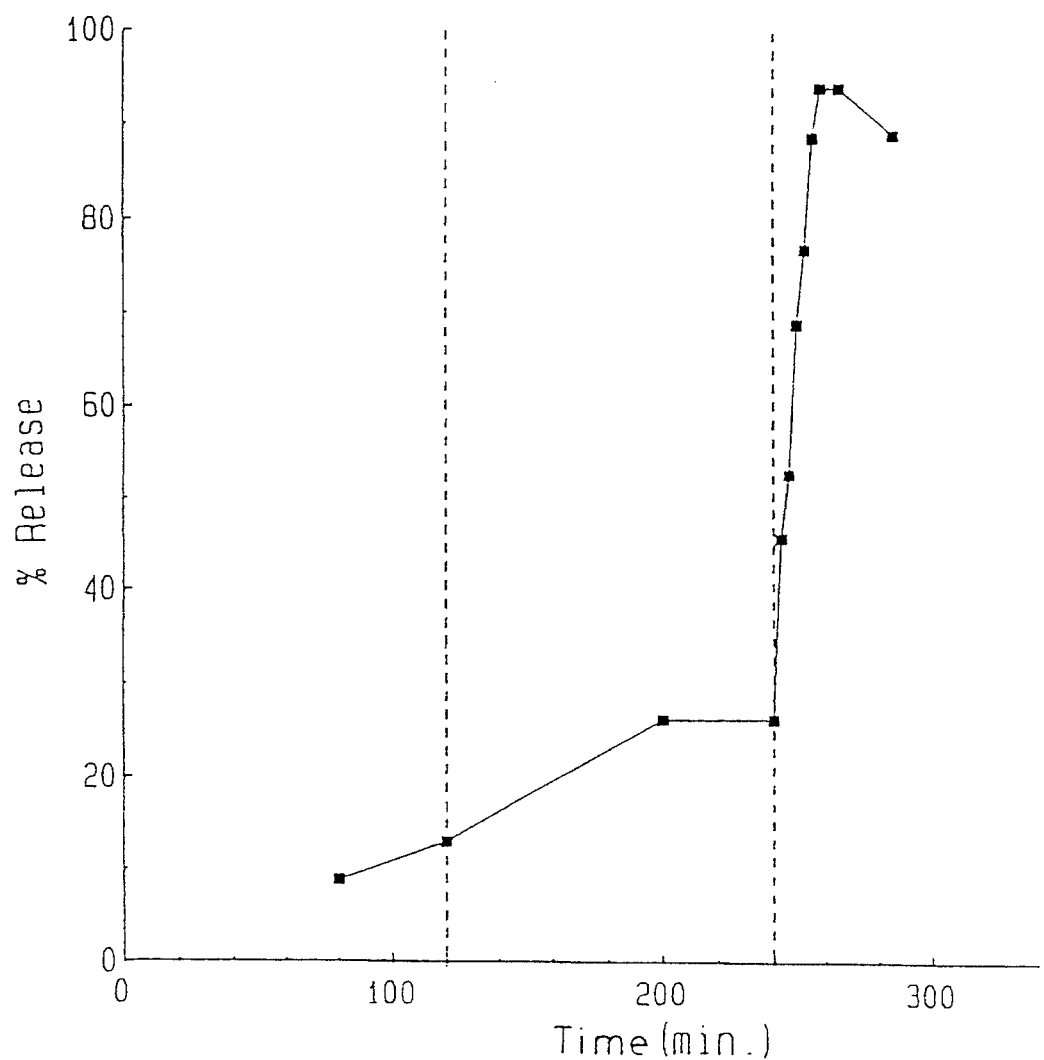

United States Patent [19]

Edman et al.

[11] Patent Number: 5,505,966
[45] Date of Patent: Apr. 9, 1996

[54] THERAPEUTICAL COMPOSITION AND PROCESS FOR ITS PREPARATION

[75] Inventors: Peter Edman, Bjärred; Kristensen Arne; Wideholt Bengt, both of Uppsala, all of Sweden

[73] Assignee: Kabi Pharmacia AB, Uppsala, Sweden

[21] Appl. No.: 958,369

[22] PCT Filed: Jul. 3, 1991

[86] PCT No.: PCT/SE91/00475

§ 371 Date: Feb. 24, 1993

§ 102(e) Date: Feb. 24, 1993

[87] PCT Pub. No.: WO92/00732

PCT Pub. Date: Jan. 23, 1992

[30] Foreign Application Priority Data

Jul. 4, 1990 [SE] Sweden ................... 9002339

[51] Int. Cl.⁶ .................. A61K 9/14; A61K 9/62
[52] U.S. Cl. .................. 424/493; 424/461; 424/456
[58] Field of Search .................. 424/484, 493, 424/479, 488, 499; 428/402, 402.24, 403; 427/213.31

[56] References Cited

U.S. PATENT DOCUMENTS

| | | | |
|---|---|---|---|
| 3,946,110 | 3/1976 | Hill | 514/161 |
| 3,959,457 | 5/1976 | Speaker et al. | 424/497 |
| 4,042,073 | 5/1977 | Shimizu et al. | 252/316 |
| 4,507,327 | 3/1985 | Ueda | 426/276 |
| 4,822,535 | 4/1989 | Gicman et al. | 264/4.3 |
| 4,915,948 | 4/1990 | Gallopo et al. | 424/499 |
| 5,051,304 | 3/1991 | David et al. | 424/493 |
| 5,118,510 | 6/1992 | Kuhrts | 424/495 |

FOREIGN PATENT DOCUMENTS

| | | |
|---|---|---|
| 0357793 | 3/1990 | European Pat. Off. . |
| 0391803 | 10/1990 | European Pat. Off. . |
| WO8704350 | 7/1987 | WIPO . |

*Primary Examiner*—Edward J. Webman
*Attorney, Agent, or Firm*—Birch, Stewart, Kolasch & Birch

[57] ABSTRACT

A colon selective pharmaceutical composition for oral delivery of one or more therapeutically active substances, comprises (i) a matrix core having the active substance or substances dispersed therein, and (ii) an outer cover layer without any active substance, said matrix core and cover layer being selectively degradable by enzymes normally occurring in the colon. A method of preparing such a colon selective pharmaceutical composition comprises the steps of mixing at least one therapeutically active substance with a matrix material to prepare a matrix core having the active substance or substances dispersed therein, and coating said matrix core with a material without any active substance therein to provide the matrix core with a drug-free protective cover layer, said matrix and cover layer materials being based upon at least one substance which is selectively degradable by enzymes in the colon.

11 Claims, 1 Drawing Sheet

THERAPEUTICAL COMPOSITION AND PROCESS FOR ITS PREPARATION

The present invention relates to a novel colon selective pharmaceutical composition as well as to a process for its preparation.

The conventionally used pharmaceutical compositions for oral delivery of drugs which are to exert their activity locally in the colon are not quite satisfactory. For example, they release a considerable amount of the active component already on their way to the colon tract and/or the release of the active component is too slow once the composition has reached the colon.

The present invention aims at overcoming the deficiencies of the prior art compositions by providing an improved colon selective composition which substantially retains the drug within the composition matrix until it reaches the colon, at which time the drug is quickly and efficiently released, as well as a process for the preparation of such a composition.

According to a first basic concept of the present invention, a pharmaceutical composition for oral delivery of a therapeutically active substance has the latter dispersed in a matrix material core, at least a substantial part of which is selectively degradable by the enzymes normally occurring in the colon, thereby providing for rapid decomposition of the matrix and momentary release of the active substance(s) dispersed therein once the composition has reached the colon.

According to a second basic concept of the invention, the matrix core is provided with a protective cover layer having no therapeutically active substance dispersed therein, which protective cover layer also is selectively degradable in the colon. Such a cover layer will serve as a protective or wear layer during the transport of the composition through the gastro-intestinal tract and prevent leakage of the active substance(s) from the matrix core into the surrounding medium.

Thus, in one aspect the present invention provides a colon selective pharmaceutical composition for oral delivery of one or more therapeutically active substances, comprising (i) a matrix core having the active substance(s) dispersed therein, and (ii) an outer cover layer without any active substance dispersed therein, said matrix core and cover layer being selectively degradable by enzymes normally occurring in the colon, such that the composition substantially will retain the active substance(s) therein until it reaches the colon, when the active substance(s) will be released.

In another aspect the present invention provides a method for the preparation of such a colon selective pharmaceutical composition for oral administration, comprising the steps of (i) mixing one or more therapeutically active substances with a matrix material to prepare a matrix core having the active substance(s) dispersed therein, and coating said matrix core with a material without any active substance dispersed therein to provide the matrix core with a drug-free protective cover layer, said matrix and cover layer materials being based upon substances selectively degradable by enzymes in the colon.

While a matrix selectively degradable by colonic enzymes will efficiently release the active substance(s) once the composition has reached the colon, the provision of a drug-free cover layer non-permeable for the active substance(s) and which is also selectively enzymatically degradable in the colon but resistant to the conditions prevailing in the stomach and small intestine, will prevent leakage of active substance from the coacervate matrix, especially if the active substance is soluble in water, and also strengthen the matrix mechanically. Such coating will thus provide for protection against both physical and chemical activity in the passage of the composition form through the upper parts of the gastro-intestinal tract.

Preferably, the matrix, and advantageously also the cover layer, are based upon one or more polysaccharides selectively degradable by enzymes in the colon. By the term "based upon" as used herein in the present context is meant that the matrix contains sufficient degradable component for the coated matrix to be efficiently disintegrated when subjected to the enzymatic attack in the colon.

When the protective cover layer comprises a polysaccharide, or a mixture of polysaccharides, which like the matrix core is capable of being selectively degraded in the colon, this or these polysaccharides may be the same as, or comprise the polysaccharide(s) forming the enzyme degradable part of the matrix core, but may also be or comprise other colon-degradable polysaccharides.

It has recently been discovered that the colonic tract contains inter alia pectinase activity, and since some pectins have been found to be useful for coacervation procedures, suitable polysaccharides for the purposes of the invention comprise such pectins and salts and derivatives thereof.

An enzymatically degradable polysaccharide based matrix core and cover layer may, in addition to such polysaccharide(s), also comprise one or more additional substances or fillers which may, but do not have to be, degradable by the enzyme systems of the colon. Exemplary of such fillers are other polysaccharides, e.g. dextrans, alginates and gum arabic, celluloses, e.g. methylcellulose, and derivatives thereof. An advantageous matrix material combination for the purposes of the invention is pectin and dextran, dextran splitting enzymes also being present in the colon.

The active substance or substances to be dispersed in the matrix may be any drug or drug combination which is desired to exert its activity in the colon, particularly for the treatment of inflammatory bowel disease, such as ulcerous colitis. As examples of such drugs may be mentioned especially anti-inflammatory steroids, but also substances like sulfasalazine, olsalazine, 5-ASA, and the like.

The composition of the invention is, however, not only useful for local delivery of therapeutical substances for activity in the colon, but also for systemic delivery of therapeutical substances for which it may be desirable that they are released in the colon, e.g. stomach irritant drugs.

In a suitable administration form, the pharmaceutical composition according to the present invention is in the form of pellets placed in a gelatine capsule.

In a preferred embodiment of the invention, the polysaccharide based matrix core containing the therapeutically active species, and preferably also the cover layer, is of coacervate type, and particularly a coacervate prepared by so-called ionotropic coacervation, as will be described in more detail below. Such a coacervate matrix and cover layer will readily provide for the desired properties, i.e., on one hand, being capable of having the drug effectively dispersed in the matrix, and, on the other hand, having such a structure that will favour the required rapid enzymatic degradation and disintegration of the matrix and cover layer when the enzyme degradable polysaccharide chains are cleaved.

Coacervation techniques for the preparation of pharmaceutical compositions have been used in the prior art, the purpose thereof, however, mainly being to provide slow-release administration forms. Encapsulation procedures for various substances using coacervation techniques are, for example, generally described in GB-B-929 406; GB-B-929 401; U.S. Pat. Nos. 3,266,987; 4,794,000 and 4,460,563.

With specific reference to ionotropic coacervation, it may be referred to, for example, FR-B-2 042 034, disclosing the production of caviar imitating products, and WO 87/04350, which discloses the separate application of two components, capable of forming a coacervate gel, to the same area of a mucous membrane to thereby achieve improved adherence. Further, EP-A-357 793 discloses slow-releasing alginic acid coacervate gel beads containing a medicament. EP-A-202 819 discloses a drug delivery system based upon a drug entrapped in a cross-linked multivalent cation alginate or carageenenate matrix. U.S. Pat. No. 4,024,073 discloses a polyvalent metal ion cross-linked polymer hydrogel for timed release of drugs and medicaments. JP-A-6104480 discloses an outer coat for soft capsules, which coat is prepared by cross-linking a polysaccharide with a bivalent cation.

A colon selective pharmaceutical composition of the invention having a coacervate matrix may thus be prepared by reacting, in the presence of the drug to be dispersed in the matrix, a cation reactive polysaccharide, capable of being degraded enzymatically in the colon, with a polyvalent cation to form a coacervate by non-covalent complexing, i.e. by forming cationic connections between the polysaccharide chains, and then coating the resulting matrix core with a drug-free cover layer, preferably also as a polysaccharide coacervate.

More particularly, such a process may comprise the steps of:

a) providing a first solution containing at least one cation reactive polysaccharide capable of being selectively degraded by enzymes in the colon, said solution having at least one therapeutically active component dispersed or dissolved therein, b) dropwise adding said first solution to a second solution containing at least one member selected from polyvalent, preferably bi- and trivalent cations to form coacervate globules of the cation reactive polysaccharide(s) complexed with said cation(s), said coacervate globules having said at least one therapeutically active component dispersed therein, and c) contacting the resulting coacervate globules with a third solution containing at least one cation reactive polysaccharide capable of being selectively degraded by enzymes in the colon, said polysaccharide(s) reacting with an excess of cations in the coacervate globules to form a coacervate cover layer thereon without said therapeutically active component, and optionally drying the resulting coacervate coated globules.

The solution in step a) above may also contain one or more enzyme degradable polysaccharides which are not cation reactive, these non-reactive polysaccharides then forming enzyme degradable building blocks entangled in the coacervate formed. The proportion of such cation non-reactive polysaccharide(s) may vary, but may well exceed that of the cation reactive one(s), the only restriction being that the latter should be present in a sufficient amount to form a coacervate structure that will keep the matrix together. In accordance with the preceding description a suitable example of such a polysaccharide is dextran or a derivative thereof.

The cation reactive enzyme degradable polysaccharide is preferably a pectin or salt or derivative thereof, such as e.g. potassium pectate.

Examples of bi- or trivalent cations that may be used in the coacervation process of the invention are $Ca^{2+}$, $Mg^{2+}$, $Al^{3+}$, $Fe^{2+}$, $Fe^{3+}$.

In the formation of an outer cover layer based upon an enzyme degradable polysaccharide or polysaccharide mixture in step c) above, the globules obtained in step b) are preferably washed before being treated with an aqueous solution containing the at least one cation reactive and colonic enzyme reactive polysaccharide. As in the case of the preparation of the drug containing matrix core, the polysaccharide solution may also contain an additional enzyme degradable polysaccharide or polysaccharide combination which is not cation reactive, as well as one or more other filler substances. In this way a spherical drug-free coacervate outer layer will result from the polysaccharides reacting with the polyvalent cations already present in the matrix, i.e. cations which have penetrated into the coacervate globules by the osmotic pressure arisen in the coacervation process and which are in excess in the globules. These cations will then be exuded from the globules and react with cation reactive polysaccharide(s) on the globule surfaces to form a coacervate shell around the globules.

A drug-containing coacervate globule or pellet having an outer drug-free polysaccharide based layer produced as described above will contain polysaccharide chains interconnected by the polyvalent cations used for the coacervation. In the stomach of a patient having a normal gastric acid function, hydrogen ions will penetrate into both the outer layer and the core of the pellet and by ion-exchange substitute hydrogen ions for the polyvalent cations, leaving the polysaccharide chains non-complexed to a great extent and more or less keeping together by sterical effects rather than by cation connections. In fact, such removal of the cation connections has been found to be highly favourable for the pellet matrix core and cover layer to be readily disintegrated in the colon when the polysaccharide chains are cleaved enzymatically and thereby provide for momentary release of the drug dispersed therein.

The process for the preparation of the coacervate pellet (the term pellet herein refers to the dried form) therefore preferably includes a post-treatment of the pellet, or the coacervate globule before it is dried to a pellet, with hydrogen ions to ensure that the enzymatic cleavage in the colon will lead to adequate decomposition of the coacervate matrix core and outer cover layer and rapid release of the drug even in patients suffering from a low content of hydrogen ions in the stomach. The degree of ion exchange will, of course, depend on the hydrogen ion concentration and the contact time. In case the pellet contains dextran, the hydrogen ion containing solution preferably also contains a sufficient concentration of dextran to prevent release of dextran from the pellet.

It will be appreciated that in a patient having an abnormally high hydrogen ion concentration in the stomach, the removal of the cation connections, especially in an outer protective coacervate layer, could be too excessive and weaken the matrix core and protective layer, respectively, thereby reducing the resistance of the pellet to mechanical damage in its passage through the stomach and small intestine. Thus, to make the outer coacervate protective layer capable of withstanding a high hydrogen ion concentration in the stomach and simultaneously increase the mechanical strength of the coacervate globule or at least the outer protective coacervate layer, a post-treatment of the, optionally hydrogen ion treated, coacervate globules with polyvalent cations may be performed prior to their being dried to pellets. By such cation treatment, which is to be carried out with a higher cation concentration than in the coacervation process, more charged $COO^-$ groups in the polysaccharide will react with the multivalent ions and in this way the polysaccharide chains will be interconnected to a higher extent. Accordingly, the more coupling points there are between the polysaccharide chains, the higher hydrogen ion concentration will the protective cover layer withstand without being weakened during the passage of the pellet through the stomach.

Such strengthening of the outer protective layer by cation treatment will, however, this being at least as important, make the layer more resistant to damages during the following processing steps, i.e. washing and drying.

In the case of, for example, a pectin coacervate, the outer protective cover layer may also be strengthened by a treatment with potassium ions, e.g. a $KCl/CaCl_2$ solution, potassium ions increasing the gel strength of pectins.

The chemical and mechanical properties of the pharmaceutical pellet produced may consequently be controlled by the above described procedures of hydrogen ion and/or cation treatment. A pellet comprising a drug-free coacervate protective coating and optionally subjected to either or both of the above post-treatments may, of course, be protected further, if desired, by the application of a conventional enteric coating. It will be appreciated that such an enteric coating applied to a pellet which has been post-treated with hydrogen ions will retain the complexing degree in the pellet unchanged during the transport thereof all the way down to the colon where the coating is dissolved and the pellet thereby is exposed to the desired enzymatic attack.

The colon selective composition of the invention may, of course, also be prepared by other methods than coacervation techniques, as will readily be realized by the skilled person.

A coacervation procedure in accordance with the invention may in a general embodiment thereof be performed by dissolving the cation reactive polysaccharide, e.g. potassium pectate (preferably low molecular esterified, i.e. part of the carboxylic groups being e.g. methyl esterified), optionally together with additional enzyme degradable polysaccharide(s) and/or non-degradable fillers, in water to form an aqueous solution thereof. The drug or drugs are then added to the solution to be dissolved or dispersed therein, whereupon the resulting solution or dispersion preferably is degassed by subjecting it to vacuum. The solution is then dropped into an aqueous or alcoholic solution containing cations of bi- or trivalent charge, the drops solidifying in the reaction between the cation reactive polysaccharide and the cations.

The spheres or globules formed hereby are then provided with a protective cover layer by treatment with a solution of a cation reactive polysaccharide, such as the above potassium pectate, optionally with the addition of some other polysaccharide(s)/polymer(s) as filler. To this end the spheres may, by way of example, be treated as follows:

1. Washing with water.
2. Treatment with an aqueous solution of potassium pectate and another polysaccharide.
3. Washing with water.
4. Treatment with a solution of bi-/trivalent cations or hydrogen ions.
5. Washing with water.
6. Optionally washing with ethanol.
7. Drying to pellets.

The resulting pellets may then optionally be treated with hydrogen ions (e.g. hydrochloric acid 0,001–10M) for more than 0.1 min., optionally with vacuum and/or pressure, whereupon they are washed with distilled water and dried. Such hydrogen ion treatment may, alternatively, be performed prior to drying the spheres to pellets.

The invention will now be described further by way of some non-limiting specific examples, reference also being made to the accompanying drawing, in which FIG. 1 is a diagram showing the drug release from colon selective drug pellets of the invention in different surroundings.

RECIPES

Examples of basic recipes for the matrix, cation solution and protective cover layer, respectively, will first be given, indicating both the specific quantities of the respective ingredients used in the following preparation examples and generally usable ranges of the ingredients.

| | | Limits |
|---|---|---|
| Basic recipe for matrix: | | |
| Distilled water | 192 g | 192 g |
| Potassium pectate | 8 g | 0.01–20% w/w of water |
| Pectin | 0 g | 0–5% w/w of water |
| Avicel (microcrystalline cellulose) | 0 g | 0–8% w/w of water |
| Dextran | 50 g | 0% w/w of water to sat. solution |
| Drug | 1 g | 0.01–50% w/w of water |
| Temperature | 0–100° C. | |
| Basic recipe No. 1 for cationic solution | | |
| Calcium chloride | 20 g | 0.001% w/w of water to sat. solution |
| Distilled water | 980 g | 980 g |
| Basic recipe No. 2 for cationic solution | | |
| Calcium chloride | 20 g | 0.001% w/w of ethanol to sat. solution |
| Ethanol | 980 g | 980 g |
| Basic recipe for protective layer | | |
| Distilled water | 192 g | 192 g |
| Potassium pectate | 1 g | 0.001–20% w/w of water |
| Pectin | 0.25 g | 0–15% w/w of water |
| Avicel | 0 g | 0–8% w/w of water |
| Dextran | 10 g | 0% to saturated aqueous solution |

EXAMPLE 1

Budesonide Composition

The basic recipe given above for the matrix is used with the exception that the amount of dextran is 20 g.

The potassium pectate, dextran and drug, here Budesonide, are thoroughly mixed. The powdery mixture obtained is added to the distilled water with vigorous stirring. The temperature is preferably maintained between 20° and 25° C. The resulting solution is stirred to dissolve or suspend all powder and is then placed under high vacuum for about 30 min., whereupon the solution is added dropwise to a 2% w/w aqueous calcium chloride solution.

The coacervate spheres formed are then coated with a protective cover using a solution prepared according to the above given basic recipe therefor. Thus, the potassium pectate, pectin and dextran are dissolved in the distilled water. After the spheres have been washed with water they are treated with the solution just prepared.

The resulting coacervate spheres are post-treated by any one of the following procedures:

1. The coacervate spheres are thoroughly washed with distilled water and dried to pellets.

2. The coacervate spheres are thoroughly washed with distilled water and shortly, 5–15 sec., with alcohol and are then allowed to dry to pellets.

3. The coacervate spheres are thoroughly washed with distilled water and the spheres are then treated with 0.001–10M hydrochloric acid, here specifically 0.1M hydrochloric acid, for more than 0.1 min., optionally under vacuum and/or pressure. The spheres are then washed and dried to pellets.

4. The coacervate spheres are washed and dried to pellets which are then treated with 0,001–10M hydrochloric acid, here specifically 0.1M hydrochloric acid, for more than 0.1 min., optionally under vacuum and/or pressure. The spheres are then washed and dried to pellets.

5. The coacervate spheres are treated with a cation solution prepared as defined in basic recipe No. 1 or 2 for the cationic solution above, for more than 0.1 min. The spheres are then washed with distilled water and optionally with ethanol and subsequently dried to pellets.

EXAMPLE 2

Budesonide Composition

A matrix is prepared from 192 g of distilled water, 16 g of potassium pectate and 1 g of Budesonide in the same way as in Example 1. The resulting coacervate spheres are then optionally post-treated in accordance with any one of the post-treatment procedures 1 to 5 in Example 1.

EXAMPLE 3

Budesonide Composition

A matrix is prepared as in Example 1 and 2, using the basic matrix recipe given above with Budesonide as the drug, except that 1 g of Avicel is included and the dextran is omitted.

EXAMPLE 4

Olsalazine Sodium Composition 8 g of potassium pectate and 1 g of olsalazine sodium are thoroughly mixed, and the powdery mixture is then added to 192 g of distilled water with vigorous stirring, suitably at a temperature between 20° and 25° C. The resulting solution is stirred such that all powder is dissolved and is subsequently placed under high vacuum for about 30 minutes. The degassed solution is then dropwise added to a 2% calcium chloride solution in 99.5% ethanol. The coacervate formed is washed with ethanol and dried to pellets. A protective coacervate cover layer is applied prior to drying. The resulting pellets may be post-treated with 0.001–10M hydrochloric acid as in post-treatment procedure 4 in Example 1.

EXAMPLE 5

Hydrocortisone Composition—In Vitro Test

A matrix was prepared as described in Example 1 from 192 g of distilled water, 8 g of cation reactive potassium pectate (Genu Pectin LM111CSZ, supplied by A/S Københavns Pektinfabrik, Copenhagen, Denmark) and 4 g of hydrocortisone. The coacervate spheres obtained were then provided with a protective cover layer as described in Example 1 using a mixture of 192 g of distilled water, 6 g of cation reactive potassium pectate (Genu Pectin LM111CSZ) and 2 g of non-reactive pectin (Genu Pectin Type DD) which mixture had been diluted with 9 times its weight of distilled water.

The resulting coated pellets were then subjected to an in vitro test designed to simulate the passage of the pellets through the gastro-intestinal tract. In this test the pellets were sequentially treated in 0.1M HCl for 120 minutes, in phosphate/citrate buffer, pH 7.0, for 120 minutes and finally in the presence of pectolyase. The hydrocortisone released to the surrounding solution was monitored during the test by UV measurements. The results are illustrated in the accompanying drawing FIG. 1. From the figure it may be seen that the release of hydrocortisone is low in 0.1M HCl (resembling the conditions in the stomach) and in phosphate/citrate buffer (resembling the conditions in the small intestine). In contrast, the release is considerably increased in the presence of pectolyase, simulating the conditions in the colon.

EXAMPLE 6

Steroid Composition

Coacervate spheres were prepared as described in Example 1 from, on one hand, a pectate solution consisting of: 200 g of distilled water, 4 g of cation reactive potassium pectate (Genn Pectin LM111CSZ, supplied by A/S Københavns Pektinfabrik, Copenhagen, Denmark), 2 g of non-reactive pectin (Genu Pectin Type DD), 8 g of Avicel, 18 g of Dextran T70 (Kabi Pharmacia AB, Uppsala, Sweden), and 3.1 g of steroid (Budesonide); and, on the other hand, a calcium chloride solution consisting of: 26.5 g of $CaCl_2 \cdot 2H_2O$, 70 g of Dextran T70, and distilled water q.s. to 1000 g. After washing with water, a protective cover layer was applied to the spheres formed by treatment, as in Example 1, with a surface polymerizing solution consisting of 200 g of distilled water and 6 g of reactive potassium pectate (Genu Pectin LM111CSZ). The mixture was diluted 1:7 prior to use. The coated spheres were then washed with water and subsequently with ethanol, dried and treated for 2 hours with a mixture of 100 g of 0.12M hydrochloric acid and 18 g of Dextran T70. After wash with water and then ethanol, the spheres were dried and filled into gelatine capsules.

We claim:

1. A colon selective pharmaceutical composition for oral delivery of one or more therapeutically active substances, comprising (i) a matrix core having the active substance or substances dispersed therein, and (ii) an outer cover layer without any active substance, wherein each of said matrix core and said cover layer is selectively degradable by colonic enzymes and is comprised of one or more polysaccharides that are selectively degradable by colonic enzymes.

2. The composition as claimed in claim 1, wherein at least one of said enzymatically degradable polysaccharides are present in the matrix core as a coacervate.

3. The composition as claimed in claim 2, wherein at least one of said matrix core and said cover layer, in addition to said coacervate forming polysaccharide, comprises one or more colonic enzyme degradable polysaccharides which are not involved in the coacervate formation.

4. The composition as claimed in claim 3, wherein said one or more additional polysaccharides is selected from the group consisting of dextrans and derivatives thereof.

5. The composition according to claim 2, wherein said coacervate is formed by cross-linking an enzymatically degradable cation-reactive polysaccharide via a polyvalent cation.

6. The composition according to claim 5, wherein said polyvalent cation is selected from the group consisting of $Ca^{2+}$, $Mg^{2+}$, $Al^{3+}$, $Fe^{2+}$, and $Fe^{3+}$.

7. The composition as claimed in claim 1, wherein said enzyme degradable polysaccharides are selected from the group consisting of pectins, salts thereof, and derivatives thereof.

8. The composition as claimed in claim 1, wherein at least one of said matrix core and said cover layer comprises a filler substance that is not enzymatically degradable in the gastro-intestinal tract.

9. A method for treating a colon comprising orally administering to a patient the pharmaceutical composition of claim 1.

10. The composition according to claim 1, wherein said matrix core is based on a first polysaccharide that is selectively degradable by colonic enzymes and said cover layer is based on a second polysaccharide that is selectively degradable by colonic enzymes and said first polysaccharide and said second polysaccharide are not the same.

11. The composition as claimed in claim 1, wherein one of said enzyme degradable polysaccharides is selected from the group consisting of dextrans and pectins.

* * * * *